(12) United States Patent
Anderson et al.

(10) Patent No.: US 11,690,726 B2
(45) Date of Patent: Jul. 4, 2023

(54) SURGICAL COMPONENT, KIT AND METHOD

(71) Applicants: DEPUY IRELAND UNLIMITED COMPANY, County Cork (IE); DEPUY SYNTHES PRODUCTS, INC., Raynham, MA (US)

(72) Inventors: James Anderson, Leeds (GB); Mahsa Avadi, Leeds (GB); Duncan Beedall, Leeds (GB); Timothy Board, Lancashire (GB); Oliver Coultrup, Leeds (GB); John Bohannon Mason, Charlotte, NC (US); Richard Patnelli, Leeds (GB); Michael Reeve, Tadcaster (GB)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 165 days.

(21) Appl. No.: 17/248,214

(22) Filed: Jan. 14, 2021

(65) Prior Publication Data
US 2022/0218489 A1    Jul. 14, 2022

(51) Int. Cl.
*A61F 2/36* (2006.01)
*A61F 2/40* (2006.01)
*A61F 2/46* (2006.01)
*A61F 2/30* (2006.01)

(52) U.S. Cl.
CPC .......... *A61F 2/3676* (2013.01); *A61F 2/4059* (2013.01); *A61F 2/4684* (2013.01); *A61F 2002/30153* (2013.01); *A61F 2002/30158* (2013.01); *A61F 2002/30214* (2013.01); *A61F 2002/3678* (2013.01); *A61F 2002/4077* (2013.01)

(58) Field of Classification Search
CPC .... A61F 2/3676; A61F 2/3662; A61F 2/4059; A61F 2/4684; A61F 2002/30841; A61F 2002/30878; A61F 2002/30879; A61F 2002/30884; A61F 2002/30892; A61F 2002/30881
See application file for complete search history.

(56) References Cited

U.S. PATENT DOCUMENTS

| 4,608,053 A * | 8/1986 | Keller ................. A61F 2/30728 |
| | | 623/23.31 |
| 4,623,349 A | 11/1986 | Lord |
| 4,664,668 A * | 5/1987 | Beck ................. A61F 2/30771 |
| | | 623/23.29 |

(Continued)

*Primary Examiner* — Alvin J Stewart

(57) ABSTRACT

A surgical component, a kit including the surgical component, and a surgical method. The surgical component includes a body portion. The surgical component also includes an elongate stem for inserting into an intramedullary canal of a patient. The elongate stem extends distally from the body portion. The elongate stem has a longitudinal axis; a proximal end; a distal end; and a plurality of splines located on an outer surface of the stem. The splines are circumferentially arranged around the stem. At least some of the splines are tapered such that each tapered spline is narrower at a distal part of that spline than at a part of that spline that is proximal with respect to the distal part. The surgical component further includes an elongate neck portion extending from the body portion at a non-zero angle with respect to the longitudinal axis of the stem.

30 Claims, 2 Drawing Sheets

(56) References Cited

U.S. PATENT DOCUMENTS

| | | | | |
|---|---|---|---|---|
| 4,944,761 | A * | 7/1990 | Stuhmer | A61F 2/36 623/23.31 |
| 5,509,935 | A * | 4/1996 | Fosco | A61F 2/3676 623/23.32 |
| 5,683,395 | A * | 11/1997 | Mikhail | A61F 2/4684 606/86 R |
| 5,766,261 | A * | 6/1998 | Neal | A61B 17/1659 606/85 |
| 6,224,634 | B1 * | 5/2001 | Keller | A61F 2/36 623/23.11 |
| 6,283,999 | B1 * | 9/2001 | Rockwood, Jr. | A61F 2/40 623/19.12 |
| 6,371,991 | B1 * | 4/2002 | Manasas | A61F 2/4607 623/22.35 |
| 7,575,603 | B2 * | 8/2009 | Bergin | A61F 2/3662 623/23.31 |
| 8,562,690 | B1 * | 10/2013 | Dickerson | A61F 2/367 623/22.44 |
| 11,364,125 | B2 * | 6/2022 | Rickels | A61F 2/3662 |
| 11,413,153 | B2 * | 8/2022 | Zhu | A61F 2/367 |
| 2003/0187510 | A1 * | 10/2003 | Hyde | A61B 17/68 623/18.12 |
| 2003/0195633 | A1 * | 10/2003 | Hyde, Jr. | A61B 17/68 623/18.12 |
| 2003/0220700 | A1 * | 11/2003 | Hammer | A61L 27/58 623/23.75 |
| 2004/0267267 | A1 * | 12/2004 | Daniels | A61B 17/1617 623/22.42 |
| 2006/0004465 | A1 * | 1/2006 | Bergin | A61F 2/3662 623/23.31 |
| 2007/0118229 | A1 * | 5/2007 | Bergin | A61F 2/30771 623/23.46 |
| 2008/0161811 | A1 * | 7/2008 | Daniels | A61B 17/1739 606/80 |
| 2009/0099662 | A1 * | 4/2009 | Splieth | A61F 2/4684 623/19.12 |
| 2009/0270860 | A1 | 10/2009 | Bergin | |
| 2011/0035021 | A1 * | 2/2011 | Bergin | A61F 2/36 623/22.42 |
| 2011/0257758 | A1 | 10/2011 | Smith | |
| 2012/0078375 | A1 * | 3/2012 | Smith | A61F 2/4014 623/20.35 |
| 2012/0095568 | A1 * | 4/2012 | Grappiolo | A61F 2/3662 623/23.26 |
| 2012/0259424 | A1 * | 10/2012 | Hood | A61F 2/4684 623/23.35 |
| 2016/0166245 | A1 | 6/2016 | Patel | |
| 2018/0228615 | A1 * | 8/2018 | Casas-Ganem | A61F 2/30771 |
| 2018/0235763 | A1 * | 8/2018 | Meneghini | A61F 2/3676 |
| 2018/0271664 | A1 * | 9/2018 | Hermle | A61F 2/30 |
| 2019/0117412 | A1 * | 4/2019 | Zimmerman | A61B 17/1668 |
| 2020/0289280 | A1 * | 9/2020 | Lefebvre | A61F 2/4014 |
| 2020/0315808 | A1 * | 10/2020 | Goldberg | A61F 2/4059 |
| 2021/0007852 | A1 * | 1/2021 | Rickels | A61F 2/3609 |
| 2022/0192682 | A1 * | 6/2022 | Fiedler | A61B 17/162 |

* cited by examiner

SURGICAL COMPONENT, KIT AND METHOD

BACKGROUND

The present specification relates to a surgical component and to a kit including a surgical component. The present specification further relates to a surgical method.

A conventional Wagner-type hip stem has a 2.5° taper along its length and a splined cross-section. The femoral canal is prepared using a reamer and then the stem impacted into position. The splines are intended to cut into the bone to provide both axial and rotational stability.

The degree of interference is a function of the relative size and insertion depths of the reamer and implant. This is a well proven technology but one drawback with current designs is that the rate of progression with each impaction is relatively constant, making it difficult for a surgeon to know when they have achieved the correct level of resistance to prevent post-operative movement. This could theoretically lead to "over-seating" leading to limb shortening or "under-seating" giving insufficient resistance postoperatively.

SUMMARY

Aspects of the present disclosure are set out in the accompanying independent and dependent claims. Combinations of features from the dependent claims may be combined with features of the independent claims as appropriate and not merely as explicitly set out in the claims.

According to an aspect of the present disclosure, there is provided a surgical component comprising:
a body portion;
an elongate stem for inserting into an intramedullary canal of a patient, wherein the elongate stem extends distally from the body portion and has:
  a longitudinal axis;
  a proximal end;
  a distal end; and
  a plurality of splines located on an outer surface of the stem, wherein the splines are circumferentially arranged around the stem, and wherein at least some of the splines are tapered such that each tapered spline is narrower at a distal part of that spline than at a part of that spline that is proximal with respect to the distal part; and
an elongate neck portion extending from the body portion at a non-zero angle with respect to the longitudinal axis of the stem.

According to another aspect of the present disclosure, there is provided a surgical method comprising using a surgical component, the surgical component comprising:
a body portion;
an elongate stem for inserting into an intramedullary canal of a patient, wherein the elongate stem extends distally from the body portion and has:
  a longitudinal axis;
  a proximal end;
  a distal end; and
  a plurality of splines located on an outer surface of the stem, wherein the splines are circumferentially arranged around the stem, and wherein at least some of the splines are tapered such that each tapered spline is narrower at a distal part of that spline than at a part of that spline that is proximal with respect to the distal part; and
an elongate neck portion extending from the body portion at a non-zero angle with respect to the longitudinal axis of the stem,
the method comprising:
  inserting the elongate stem into an intramedullary canal of a patient.

The arrangement of the tapered splines can provide a varying insertion resistance as the stem is inserted into the intramedullary canal. This can provide the surgeon (or impaction system, where a Surgical Automated System (such as KINCISE™) is used) with haptic feedback as the stem is inserted. The haptic feedback may, for instance, be used to guide the surgeon or impaction system as to when the desired seating depth of the surgical component has been reached.

The stem and/or the elongate neck portion may be integrally formed with the body portion. Alternatively, in other embodiments, the stem and/or the elongate neck portion may be detachable from the body portion. This can allow a modular construction of the surgical component to be achieved, in which differently sized modules (e.g. a larger or smaller stem and/or elongate neck) can be selected according to the procedure to be performed and attached to the body portion.

Each spline may have a distal end and a proximal end. At least some of the tapered splines may taper along their full length from the proximal and to the distal end thereof.

The splines of at least some of the tapered splines may each have a distal region and a proximal region. Those splines may be tapered in their distal region and may have a constant width in their proximal region. It is also envisaged that those splines may alternatively be tapered in their proximal region and may have a constant width in their distal region. In each spline having a tapered part in a distal (or proximal) region and a part having a constant width in a proximal (or distal) region, an interface between the distal region and the proximal region proximal region of that spline may be located proximally with respect to a fixation region of the stem. The non-tapering of the splines in the proximal (or distal) regions of the splines may prevent overcrowding of the splines at the proximal end of the stem. This may, for instance, allow the tapering to be more aggressive in the distal (or proximal) regions of the splines.

The surgical component may include a plurality of further splines circumferentially arranged around the stem.

The splines may be wider than the further splines for a majority of the length of the splines. The splines may act as primary splines, which provide all or the majority of the insertion resistance, while the further splines may act as secondary splines, which come into contact with the side walls of the intramedullary canal as the desired seating depth of the surgical component is reached.

Alternatively, the splines may be narrower than the further splines for a majority of the length of the splines.

The splines and further splines may be alternately arranged around a circumference of the stem. This can provide a surgical component having a stem which is well balanced around the circumference of the stem. For instance, this can prevent tilting of surgical component as the stem is inserted, the tilting being associated with varying insertion resistance around the circumference of the stem.

At least some of the further splines may have a constant width along their full length.

At least some of the further splines may be tapered such that each tapered further spline is narrower at a distal part of that further spline than at a part of that further spline that is proximal with respect to the distal part.

The further splines may be taller than the splines, measured from the longitudinal axis.

Alternatively, further splines may be less tall than the splines, measured from the longitudinal axis.

At least some of the splines and/or further splines may have a cross-sectional shape in a plane perpendicular to the longitudinal axis which is trapezoidal, rectangular or radiused.

The elongate stem may be tapered to be wider at its proximal end than at its distal end. The tapering of the stem and the tapering of the splines may combine to produce the varying insertion resistance as the stem is inserted into the intramedullary canal, providing the aforementioned haptic feedback to the surgeon (or impaction system, where a Surgical Automated System (such as KINCISE™) is used).

The surgical component may be a trial component, such as a trial component for trialling prior to installation of a femoral implant or a humeral implant.

The surgical component may be a broach. The broach may be used prior to installation of a femoral implant or a humeral implant.

The surgical component may be a femoral implant. The method may thus include inserting the stem into an intramedullary canal of a femur.

The surgical component may be a humerus (shoulder) implant. The method may thus include inserting the stem into an intramedullary canal of a humerus.

According to a further aspect of the present disclosure, there is provided a surgical kit including a surgical component of the kind set out above.

The method may include receiving haptic feedback while inserting the stem into the intramedullary canal. The haptic feedback may be associated with increasing resistance to insertion provided by the tapered splines as the stem is inserted.

During insertion of the stem into the intramedullary canal, the further splines may come into contact with bone defining sidewalls of the intramedullary canal immediately prior to achieving a desired seating depth of the surgical component.

BRIEF DESCRIPTION OF THE DRAWINGS

Embodiments of this disclosure will be described hereinafter, by way of example only, with reference to the accompanying drawings in which like reference signs relate to like elements and in which.

DETAILED DESCRIPTION

Embodiments of this disclosure are described in the following with reference to the accompanying drawings.

Figures 1A, 1B, 1C:
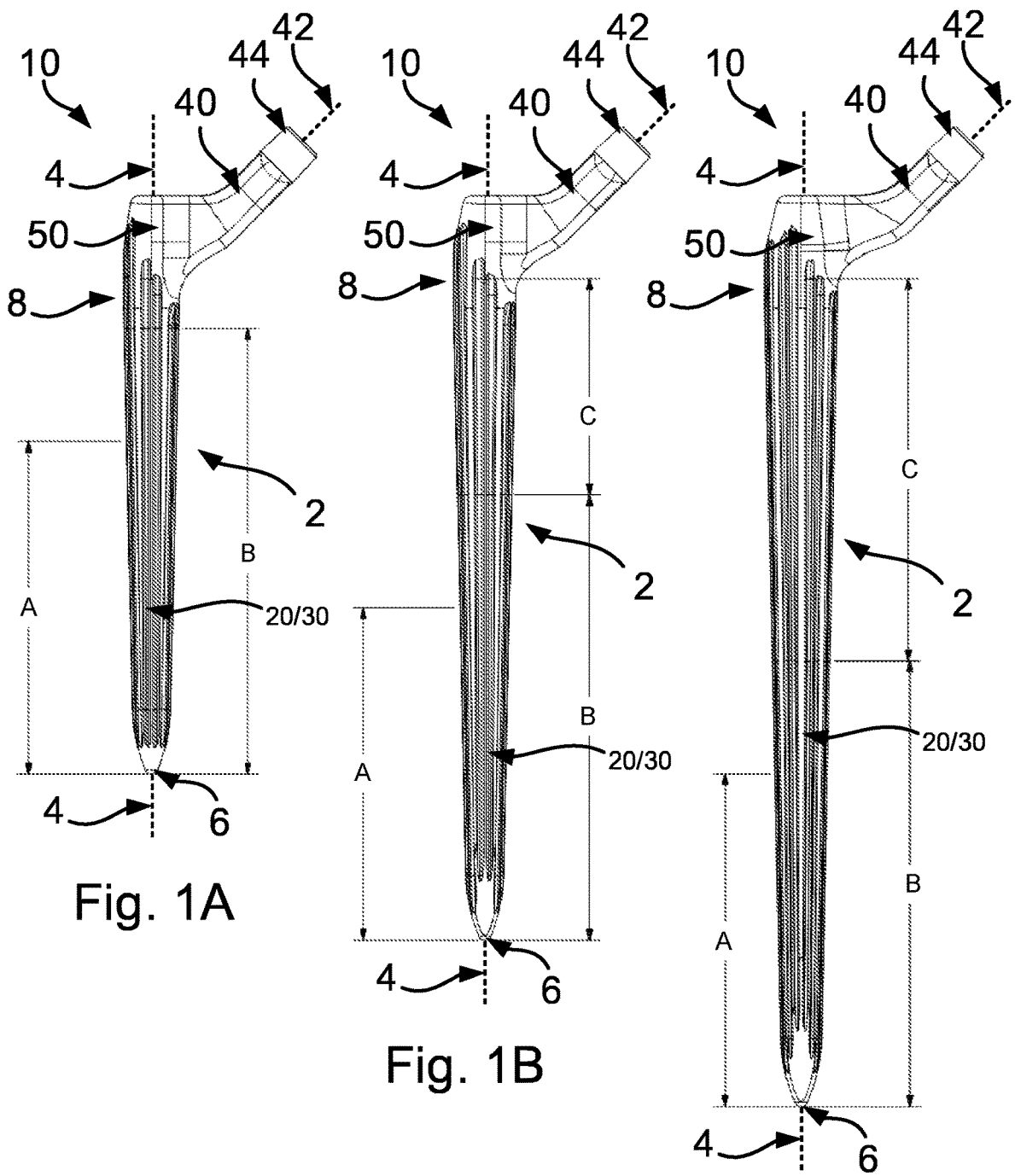
FIGS. 1A, 1B and 1C each show a surgical component comprising a surgical implant according to an embodiment of this disclosure.

FIGS. 1A, 1B and 1C each show a surgical component according to an embodiment of this disclosure. The surgical components shown in FIG. 1A-1C are surgical implants 10. Each implant 10 in the embodiments shown in FIGS. 1A-1C is designed to be installed in the femur of a patient during hip surgery. However, it is envisaged that embodiments of this disclosure may instead apply to a humeral implant for shoulder surgery. The configuration of the implant in such embodiments may be substantially as described below (particularly in relation to the splines and/or further splines), although the overall size and shape of the surgical implant would be configured to allow it to be installed in a humerus instead of a femur.

Similarly, it is envisaged that in some embodiments of this disclosure, the surgical component may be a broach. The broach may be sized and shaped for use in either hip or shoulder surgery.

Similarly, it is envisaged that in some embodiments of this disclosure, the surgical component may be a trial component. The trial component may be used in a trialling procedure prior to installation of a femoral or a humeral implant.

Each surgical implant 10 has a body portion 50, an elongate stem 2 and an elongate neck portion 40.

In the embodiments shown in FIGS. 1A-1C, the stem 2 and the elongate neck portion 40 are integrally formed with the body portion 50. Alternatively, in other embodiments, the stem 2 and/or the elongate neck portion 40 may be detachable from the body portion 50. This can allow a modular construction of the surgical component to be achieved, in which differently sized modules (e.g. a larger or smaller stem 2 and/or elongate neck portion 40) can be selected according to the procedure to be performed and attached to the body portion 50.

Note that the stems 2 in FIGS. 1A-1C are of different lengths, according to the requirements of the surgical procedure in which they may be used. Thus, the stem, 2 in FIG. 1B is longer than the stem 2 in FIG. 1A, and the stem 2 in FIG. 1C is longer than the stem 2 in FIG. 1B.

To install the implant 10, the femur (or the humerus, in the case of shoulder surgery) may first be prepared by cutting away the femoral neck, accessing the intramedullary canal and then reaming the intramedullary canal until it is appropriately shaped to receive the stem 2. The stem 2 may then be inserted into the intramedullary canal.

The stem 2 in each embodiment has a distal end 6 and a proximal end 8. The distal end 6 of the stem 2 may form a tip of the surgical implant 10. The proximal end 8 of the stem 2 joins the body portion 50. As shown in FIGS. 1A-1C, the stem 2 may be tapered such that it is wider at its proximal end 8 than at its distal end 6. The taper angle of the stem 2 may, for instance, be around 2.5°.

The stem 2 has a longitudinal axis 4, along which the stem 2 extends. When the surgical implant 10 is installed, the longitudinal axis 4 may generally align with a longitudinal axis of the femur (or the humerus, in the case of shoulder surgery).

The elongate neck portion 40 extends from the body portion 50 along a neck axis 42 of the surgical implant 10. As may be seen in FIGS. 1A-1C, the neck axis 42 is set at a non-zero with respect to the longitudinal axis 4 of the stem 2, to allow the elongate neck portion 40 to emulate the neck of the femur (or the humerus, in the case of shoulder surgery) when the surgical implant 10 is installed.

The elongate neck portion 40 may have a proximal end 44 and a distal end. The distal end of the elongate neck portion 40 may join with the body portion 50. The proximal end 44 of the elongate neck portion 40 may include a connection feature or connection features for attaching a femoral head implant (or humeral head implant, in the case of shoulder surgery) to the surgical implant 10. It is also envisaged that the proximal end 44 may be integrally formed with a femoral head part.

The stem 2 has a plurality of splines 20/30. As will be described in more detail below in relation to FIG. 2, the splines 20/30 are located on an outer surface of the stem 2.

Figure 2:
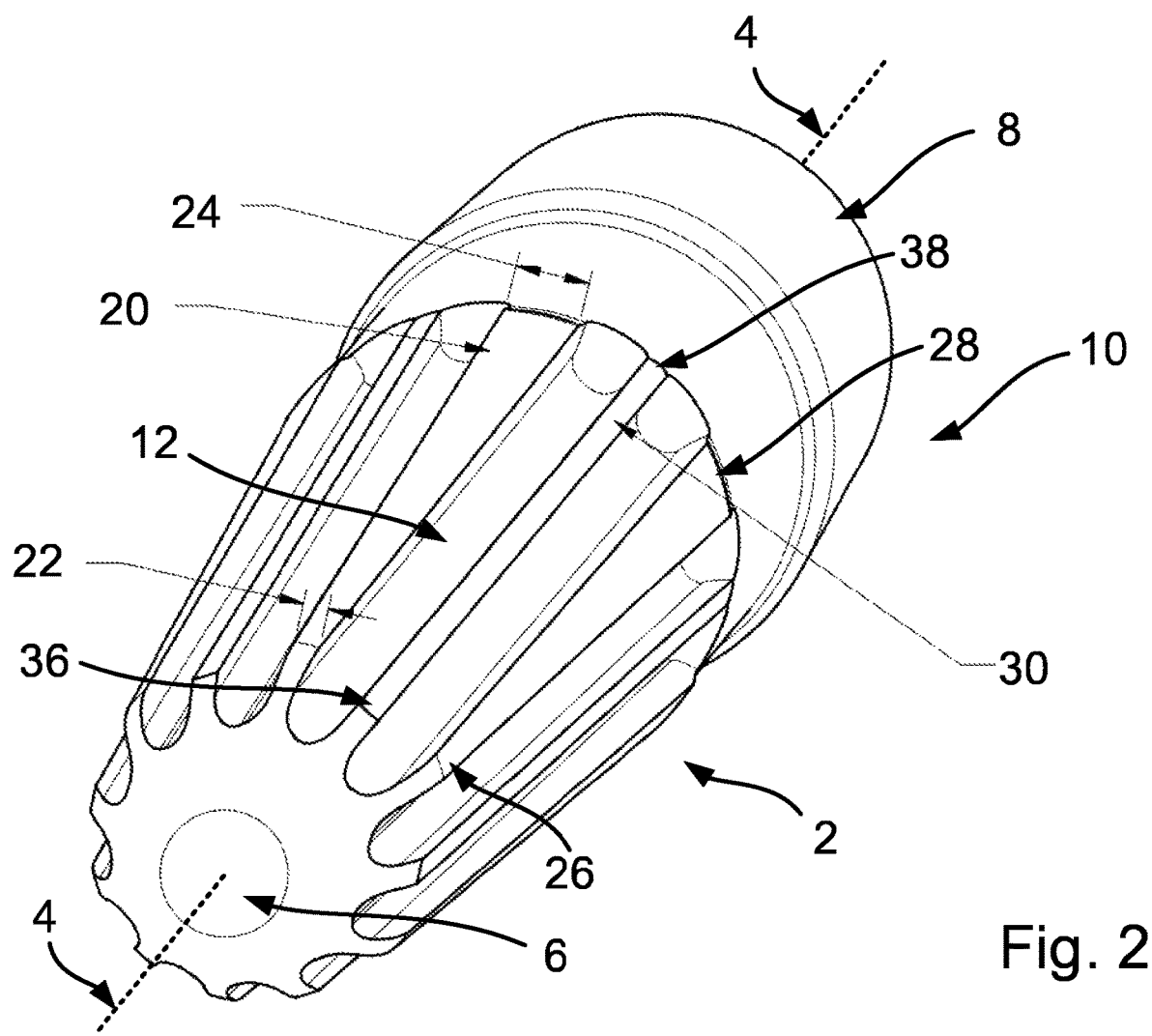
FIG. 2 shows the stem of a surgical implant according to an embodiment of this disclosure.

FIG. 2 shows a stem 2 of a surgical implant 10 of the kind shown in FIGS. 1A-1C according to an embodiment of this disclosure.

In this embodiment, the stem 2 includes a plurality of splines 20. The splines 20 are circumferentially arranged around the stem 2. Each spline 20 has a distal end 26 and a proximal end 28. As can be seen in FIG. 2, the splines 20 are tapered. In particular, each spline 20 is tapered such that it is narrower at a distal part of that spline 20 than at a part of that spline 20 that is proximal with respect to the distal part. For instance, in FIG. 2, note that the width of each spline 20 is narrower at location 22 than at location 24.

In this embodiment, the stem 2 also includes a number of optional further splines 30. The further splines 30 are also circumferentially arranged around the stem 2. Each further spline 30 has a distal end 36 and a proximal end 38.

In general, the further splines 30 may be configured (shaped) differently to the splines 20 in terms of their length, height, width, cross sectional shape and/or tapering (or lack of tapering).

In FIG. 2, the splines 20 and the further splines 30 may be arranged alternately around the circumference of the stem 2, although this is not essential. Each spline 20 and/or 30 may be separated from its nearest neighbour splines 20 and/or 30 by an intervening trough 12.

In this embodiment, each further spline 30 has a substantially constant width along its length. However, it is also envisaged that the further splines 30 may be tapered. Thus, each further spline 30 may be tapered such that it is narrower at a distal part of that further spline 30 than at a part of that further spline 30 that is proximal with respect to the distal part. Accordingly, it is envisaged that any of the tapered configurations described herein in relation to the splines 20 may also be applied to the further splines 30.

The splines 20 and/or the further splines 30 may extend substantially longitudinally along the stem 2. The splines 20 and/or the further splines 30 may extend along substantially a full length of the stem 2. As shown in FIG. 2 however, the splines 20 and/or the further splines 30 may distally terminate just short of the tip formed by the distal end 6 of the stem 2. The splines 20 and/or the further splines 30 may proximally terminate at the proximal end 8 of the stem 2, but it is also envisaged that the splines 20 and/or the further splines 30 may proximally terminate at a position located distally with respect to the proximal end 8 of the stem 2. As may be seen in FIGS. 1A-1C, it is further envisaged that at least some of the splines 20 and/or the further splines 30 may extend proximally beyond the proximal end 8 of the stem 2, such that they proximally terminate on the body portion 50 of the surgical implant 10. It is also envisaged that the further splines 30 may have a different length to the splines 20. For instance, the further splines 30 may proximally terminate either proximally or distally with respect to the splines 20 and/or the further splines 30 may distally terminate either proximally or distally with respect to the splines 20.

In FIG. 2, the splines 20 taper consistently along their length. However, it is envisaged that the tapering of the splines 20 may vary or even halt at certain points along their length.

For instance, in some embodiments, the degree of tapering along a tapered part of each spline 20 may vary. In one such example, the tapering of each spline 20 may be gradual at or near the distal end 26 and increase at one or more locations along that spline 20. This arrangement may also be reversed, such that the tapering of each spline 20 may be relatively rapid at or near the distal end 26 and decrease at one or more locations along that spline 20. These changes may provide changes in the haptic feedback provided to the surgeon (or impaction system, where a Surgical Automated System (such as KINCISE™) is used) as the stem 2 is inserted into the intramedullary canal (the haptic feedback provided by the splines 20 and/or the further splines 30 with be described in detail below).

In one or more embodiments, at least some of the splines 20 may include non-tapered regions. For instance, in one embodiment, at least some of the splines 20 each have a distal region and a proximal region, and those splines 20 may be tapered in their distal region and have a constant width in their proximal region. Alternatively, those splines 20 may be tapered in their proximal region and have a constant width in their distal region.

Returning briefly to FIGS. 1A-1C, note that in each Figure, a fixation region of the stem 2 of each implant 10 is indicated by the arrows labelled A. Also in FIGS. 1B-1C, a tapered region of the splines 20 is generally indicated by the arrow labelled B and a non-tapered region of the splines 20 is generally indicated by the arrow labelled C. Note that in each case, the transition from the tapered region B to the non-tapered region C is located proximally with respect to a most proximal part of the fixation region of the stem 2 labelled A (this may also be the case in embodiments in which the splines 20 are tapered in their proximal region and have a constant width in their distal region). In the embodiment of FIG. 1A, the splines taper along their complete length (hence FIG. 1A includes a region labelled B, but no region labelled C), The transition from the tapered region to the region of constant width may provide haptic feedback to the surgeon (or impaction system, where a Surgical Automated System (such as KINCISE™) is used) as will be described below. Moreover, the provision of the non-tapered regions towards the proximal ends 28 of the splines 20 may prevent overcrowding of the splines towards the proximal end 8 of the stem 2 (particularly in longer stems 2 of the kind shown in FIGS. 1B and 1C) and/or may allow the tapering in the distal regions (or proximal regions) of the splines 20 to be more rapid.

Figure 3:
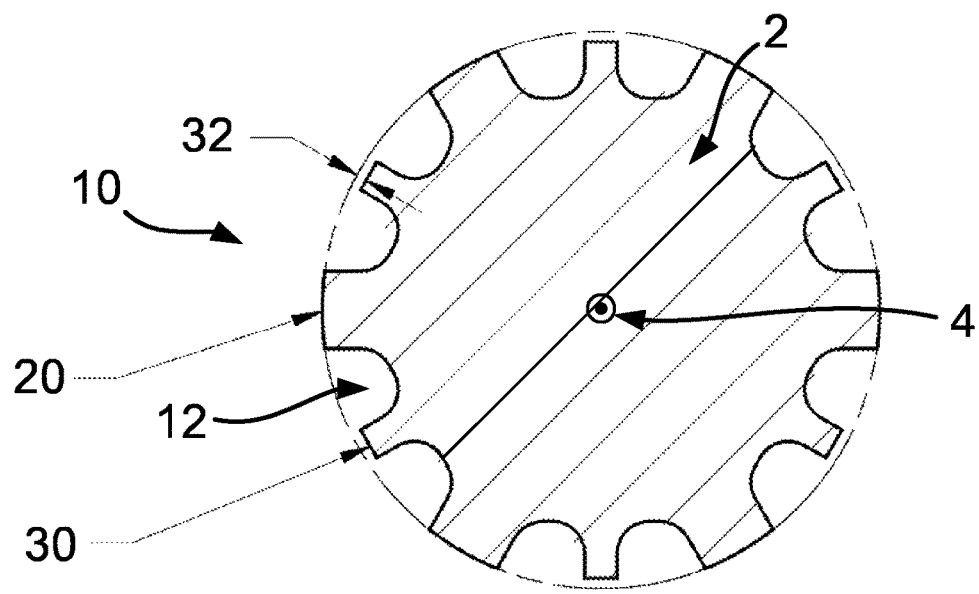
FIG. 3 shows a cross section of the surgical implant of FIG. 2, through a plane perpendicular to a longitudinal axis of the stem.

In accordance with embodiments of this disclosure, the splines 20 may be wider than the further splines 30 for a majority of the length (including the complete length) of the splines 20. An example of such a configuration is shown in FIGS. 2 and 3. However, it is also envisaged that this configuration may be reversed, such that the splines 20 are narrower than the further splines 30 for a majority of the length (including the complete length) of the splines 20.

FIG. 3 shows a cross section of the stem 2 of FIG. 2, through a plane perpendicular to a longitudinal axis 4. In this embodiment, it can be seen that the further splines 30 are less tall than the splines 20, measured radially outward from the longitudinal axis 4. The difference in height between the splines 20 and the further splines 30 (labelled using reference numeral 32 in FIG. 3) may in the region of 0.2-0.5 mm. In the present embodiment, the difference in height 32 is about 0.25 mm.

This configuration can cause the further splines 30 to come into contact with the sidewalls of the intramedullary canal later than the splines 20. This may provide the surgeon (or impaction system, where a Surgical Automated System (such as KINCISE™) is used) with further haptic feedback, as will be described below. It is envisaged that this configuration may be reversed, such that the further splines 30 are taller than the splines 20, measured radially outward from the longitudinal axis 4.

In accordance with embodiments of this disclosure, the splines 20 and/or the further splines 30 may have a cross sectional shape (i.e. in a plane perpendicular to the longitudinal axis) which is trapezoidal, rectangular (e.g. see FIG. 3) or radiused.

In accordance with embodiments of this disclosure, the maximum widths of the splines 20 and/or the further splines 30 may be around 2.8 mm, or more preferably no wider than 2*mm*. The taper angle of the tapered (parts of) the splines 20 and/or the further splines 30 may be around 1°.

According to embodiments of this disclosure, there may be provided a surgical kit. The surgical kit may include one or more surgical implants 10 of the kind described herein. The surgical kit may also include other components such as surgical implants or surgical tools.

As mentioned previously, the configurations of the splines 20 and/or the further splines 30 described herein may provide haptic feedback to the surgeon (or impaction system, where a Surgical Automated System (such as KINCISE™) is used) as the stem 2 is being inserted into the intramedullary canal of a femur (or humerus, in the case of shoulder surgery).

In embodiments in which the stem 2 of the surgical implant 10 includes the splines 20 but not the further splines 30, the tapering of the splines 20 may provide haptic feedback to the surgeon (or impaction system, where a Surgical Automated System (such as KINCISE™) is used) as follows. The surgeon may hold the surgical implant (e.g. at the body portion 50 and/or the elongate neck portion 40) while manually inserting the stem 2 into the pre-prepared intramedullary canal. When a Surgical Automated System (such as KINCISE™) is used, the implant 10 may instead be attached to an impaction system for insertion of the stem 2. As the stem 2 is inserted, the splines 20 eventually come into contact with, and begin to dig into the side walls of the intramedullary canal. Friction between the splines 20 and the sidewalls gives rise to a force which resists the further insertion of the stem 2. Owing to the tapering of the splines 20, this resistive force increases as the depth of the stem 2 inside the intramedullary canal increases. This increasing resistance to insertion of the stem 2 provides haptic feedback to the surgeon (or impaction system, where a Surgical Automated System (such as KINCISE™) is used) regarding the position of the stem 2 within the intramedullary canal and can, for example, allow the surgeon (or impaction system) to determine when a desired seating position of the surgical implant 10 within the femur (or the humerus, in the case of shoulder surgery) is being approached and/or has been reached.

In embodiments in which the stem 2 of the surgical implant 10 includes the further splines 30, The haptic feedback provided to the surgeon (or impaction system, where a Surgical Automated System (such as KINCISE™) is used) depends upon not only of the shape and configuration of the splines 20 and of the further splines 30, but also on the differences in shape and configuration of the splines 20 and further splines 30.

Assuming that the splines 20 are taller than the further splines 30, the haptic feedback provided by the splines 20 may be substantially as described above in relation to embodiments not including the further splines 30, at least until the further splines 30 come into contact with the side walls of the intramedullary canal. This is because when the further splines 30 are less tall than the splines 20 (e.g. as shown in FIG. 3), the further splines 30 will come into contact with the side walls of the intramedullary canal sometime after the splines 20 have contacted the side walls, and because the further splines 30 do not contribute to the resistive force against further insertion of the stem 2 until they contact the sidewalls. At some point during insertion of the stem 2, the further splines will nevertheless come into contact with the sidewalls. At this point there will be a step change in the resistance force opposing further insertion of the stem 2. This step change may provide the surgeon (or impaction system, where a Surgical Automated System (such as KINCISE™) is used) with further haptic feedback regarding the position of the stem 2 within the intramedullary canal. For instance, in accordance with embodiments of this disclosure, the difference in height between the splines 20 and the further splines 30 maybe chosen such the further splines 30 contact the side walls of the intramedullary canal just before the desired seating position is reached. A typical difference in height of the splines 20 and further splines 30 would be in the region of 0.2-0.5 mm.

As mentioned previously, the further splines 30 may themselves be tapered in any of the ways described herein in the context of the splines 20. Accordingly, once the further splines 30 have contacted the side walls of the intramedullary canal, the contribution to the overall resistive force opposing further insertion of the stem 2, which is provided by the further splines 30, may itself vary with insertion depth, in much the same way as that described above in relation to the splines 20.

The further splines 30 may, in some embodiments, be taller than the splines 20. In such embodiments, the further splines 30 would contact the side walls of the intramedullary canal before the splines 20. In embodiments in which the further splines 30 non-tapering and the further splines 30 are taller than the splines 20, the further splines 30 may provide a relatively constant resistive force to further insertion of the stem 2 until the splines 20 contact the sidewalls. In such embodiments, the step change in resistive force associated with the initial contact of the splines 20 with the side walls may provide haptic feedback to the surgeon (or impaction system, where a Surgical Automated System (such as KINCISE™) is used) that the correct seating position of the stem 2 is being approached. Similar considerations also apply where the further splines 30 are taller than the splines 20 and are in some way tapered, albeit that the contribution to the overall insertion resistance provided by the tapered further splines would also change with the insertion depth of the stem 2.

In embodiments including the further splines 30, the relative contributions to the overall resistive force opposing further insertion of the stem 2 at a given insertion depth may also be determined by selectively tailoring the differences in height, width, cross-sectional shape and/or taper angle of the splines 20 and the further splines 30.

According to embodiments of this disclosure, there may be provided a surgical method. The method may, for instance, form part of a hip (or shoulder) replacement or revision procedure. In general, the method may comprise the installation of a surgical component of the kind described herein.

To use the component, the stem 2 (e.g. the stem 2 of an implant 10 of the kind described above) may be inserted into the intramedullary canal of the patient's femur (or humerus, in the case of shoulder surgery). As noted previously, insertion of the stem 2 may be preceded by preparatory step such as removing the neck and head of the femur (or the humerus, in the case of shoulder surgery) and reaming the intramedullary canal to size it for receipt of the stem 2.

As the stem 2 is being inserted, the surgeon (or impaction system, where a Surgical Automated System (such as KIN- CISE™) is used) may receive haptic feedback of the kinds described above. As such, the haptic feedback may, for instance, be associated with the increasing resistance to insertion provided by the splines 20 (and possibly also the further splines 30) as the stem 2 is inserted, and/or may be associated with the further splines 30 coming into contact with bone defining sidewalls of the intramedullary canal immediately prior to achieving a desired seating depth of the implant.

Accordingly, there has been described a surgical implant, a kit including the surgical implant, and a surgical method. The surgical implant includes a body portion. The surgical implant also includes an elongate stem for inserting into an intramedullary canal of a patient. The elongate stem extends distally from the body portion. The elongate stem has a longitudinal axis; a proximal end; a distal end; and a plurality of splines located on an outer surface of the stem. The splines are circumferentially arranged around the stem. At least some of the splines are tapered such that each tapered spline is narrower at a distal part of that spline than at a part of that spline that is proximal with respect to the distal part. The surgical implant further includes an elongate neck portion extending from the body portion at a non-zero angle with respect to the longitudinal axis of the stem.

Aspects of the present disclosure are set out in the following series of numbered clauses.
1. A surgical component comprising:
   a body portion;
   an elongate stem for inserting into an intramedullary canal of a patient, wherein the elongate stem extends distally from the body portion and has:
      a longitudinal axis;
      a proximal end;
      a distal end; and
      a plurality of splines located on an outer surface of the stem, wherein the splines are circumferentially arranged around the stem, and wherein at least some of the splines are tapered such that each tapered spline is narrower at a distal part of that spline than at a part of that spline that is proximal with respect to the distal part; and
   an elongate neck portion extending from the body portion at a non-zero angle with respect to the longitudinal axis of the stem.
2. The surgical component of clause 1, wherein each spline has a distal end and a proximal end, and wherein at least some of the tapered splines each taper along their full length from the proximal and to the distal end thereof.
3. The surgical component of clause 1 or clause 2, wherein at least some of the tapered splines each have a distal region and a proximal region, wherein:
   those splines are tapered in their distal region and have a constant width in their proximal region; or
   those splines are tapered in their proximal region and have a constant width in their distal region.
4. The surgical component of clause 3, wherein, in each spline having a tapered part and a part having a constant width, an interface between the distal region and the proximal region of that spline is located proximally with respect to a fixation region of the stem.
5. The surgical component of any preceding clause, comprising a plurality of further splines circumferentially arranged around the stem.
6. The surgical component of clause 5, wherein the splines are wider than the further splines for a majority of the length of the splines.
7. The surgical component of clause 5, wherein the splines are narrower than the further splines for a majority of the length of the splines.
8. The surgical component of any of clauses 5 to 7, wherein the splines and further splines are alternately arranged around a circumference of the stem.
9. The surgical component of any of clauses 5 to 8, wherein at least some of the further splines have a constant width along their full length.
10. The surgical component of any of clauses 5 to 9, wherein at least some of the further splines are tapered such that each tapered further spline is narrower at a distal part of that further spline than at a part of that further spline that is proximal with respect to the distal part.
11. The surgical component of any of clauses 5 to 10, wherein the further splines are taller than the splines, measured from the longitudinal axis.
12. The surgical component of any of clauses 5 to 10, wherein the further splines are less tall than the splines, measured from the longitudinal axis.
13. The surgical component of any preceding clause, wherein at least some of the splines and/or further splines have a cross-sectional shape in a plane perpendicular to the longitudinal axis which is trapezoidal, rectangular or radiused.
14. The surgical component of any preceding clause, wherein the elongate stem is tapered to be wider at its proximal end than at its distal end.
15. The surgical component of any preceding clause, wherein the component is:
   a femoral implant,
   a humeral implant.
   a trial component; or
   a broach.
16. A surgical kit including a surgical component according to any preceding clause.
17. A surgical method comprising using a surgical component, the surgical component comprising:
   a body portion;
   an elongate stem for inserting into an intramedullary canal of a patient, wherein the elongate stem extends distally from the body portion and has:
      a longitudinal axis;
      a proximal end;
      a distal end; and
      a plurality of splines located on an outer surface of the stem, wherein the splines are circumferentially arranged around the stem, and wherein at least some of the splines are tapered such that each tapered spline is narrower at a distal part of that spline than at a part of that spline that is proximal with respect to the distal part; and
   an elongate neck portion extending from the body portion at a non-zero angle with respect to the longitudinal axis of the stem,
   the method comprising:
   inserting the elongate stem into an intramedullary canal of a patient.
18. The surgical method of clause 17, further comprising receiving haptic feedback while inserting the stem into the intramedullary canal, wherein the haptic feedback is associated with increasing resistance to insertion provided by the tapered splines as the stem is inserted.
19. The surgical method of clause 17 or clause 18, wherein each spline has a distal end and a proximal end, and wherein at least some of the tapered splines each taper along their full length from the proximal and to the distal end thereof.

20. The surgical method of any of clause 17 to 19, wherein at least some of the tapered splines each have a distal region and a proximal region, wherein:
those splines are tapered in their distal region and have a constant width in their proximal region; or
those splines are tapered in their proximal region and have a constant width in their distal region.

21. The surgical method of clause 20, wherein in each spline having a tapered part and a part having a constant width, an interface between the distal region and the proximal region proximal region of that spline is located proximally with respect to a fixation region of the stem.

22. The surgical method of any of clauses 17 to 21, the stem comprising a plurality of further splines circumferentially arranged around the stem.

23. The surgical method of clause 22, wherein during said insertion of the stem into the intramedullary canal, the further splines come into contact with bone defining sidewalls of the intramedullary canal immediately prior to achieving a desired seating depth of the component.

24. The surgical method of clause 22 or clause 23, wherein the splines are wider than the further splines for a majority of the length of the splines.

25. The surgical method of clause 22 or clause 23, wherein the splines are narrower than the further splines for a majority of the length of the splines.

26. The surgical method of any of clauses 22 to 25, wherein the splines and further splines are alternately arranged around a circumference of the stem.

27. The surgical method of any of clauses 22 to 26, wherein at least some of the further splines have a constant width along their full length.

28. The surgical method of any of clauses 22 to 27, wherein at least some of the further splines are tapered such that each tapered further spline is narrower at a distal part of that further spline than at a part of that further spline that is proximal with respect to the distal part.

29. The surgical method of any of clauses 22 to 28, wherein the further splines are taller than the splines, measured from the longitudinal axis.

30. The surgical method of any of clauses 22 to 28, wherein the further splines are less tall than the splines, measured from the longitudinal axis.

31. The surgical method of any of clauses 17 to 30, wherein at least some of the splines and/or further splines have a cross-sectional shape in a plane perpendicular to the longitudinal axis which is trapezoidal, rectangular or radiused.

32. The surgical of any of clauses 17 to 31, wherein the elongate stem is tapered to be wider at its proximal end than at its distal end.

33. The surgical method of any of clauses 17 to 32, wherein the surgical component is a trial implant or a broach.

34. The surgical method of any of clauses 17 to 32, wherein the surgical component is a femoral implant, and wherein the method comprises inserting the stem into an intramedullary canal of a femur.

35. The surgical method of any of clauses 17 to 32, wherein the surgical component is a humeral implant, and wherein the method comprises inserting the stem into an intramedullary canal of a humerus.

Although particular embodiments of this disclosure have been described, it will be appreciated that many modifications/additions and/or substitutions may be made within the scope of the claims.

The invention claimed is:

1. A surgical component comprising:
a body portion;
an elongate stem for inserting into an intramedullary canal of a patient, wherein the elongate stem extends distally from the body portion and has:
a longitudinal axis;
a proximal end;
a distal end; and
a plurality of splines located on an outer surface of the stem, wherein the splines are circumferentially arranged around the stem, and wherein at least some of the splines are tapered such that each tapered spline is narrower at a distal part of that spline than at a part of that spline that is proximal with respect to the distal part;
a plurality of further splines circumferentially arranged around the stem wherein the splines are wider than the further splines for a majority of the length of the splines; and
an elongate neck portion extending from the body portion at a non-zero angle with respect to the longitudinal axis of the stem.

2. The surgical component of claim 1, wherein each spline has a distal end and a proximal end, and wherein at least some of the tapered splines each taper along their full length from the proximal end to the distal end thereof.

3. The surgical component of claim 1, wherein at least some of the tapered splines each have a distal region and a proximal region, wherein:
those splines are tapered in their distal region and have a constant width in their proximal region; or
those splines are tapered in their proximal region and have a constant width in their distal region.

4. The surgical component of claim 3, wherein, in each spline having a tapered part and a part having a constant width, an interface between the distal region and the proximal region of that spline is located proximally with respect to a fixation region of the stem.

5. The surgical component of claim 1, wherein the splines and further splines are alternately arranged around a circumference of the stem.

6. The surgical component of claim 1, wherein at least some of the further splines have a constant width along their full length.

7. The surgical component of claim 1, wherein at least some of the further splines are tapered such that each tapered further spline is narrower at a distal part of that further spline than at a part of that further spline that is proximal with respect to the distal part.

8. The surgical component of claim 1, wherein the further splines are taller than the splines, measured from the longitudinal axis.

9. The surgical component of claim 1, wherein the further splines are less tall than the splines, measured from the longitudinal axis.

10. The surgical component of claim 1, wherein at least some of the splines and/or further splines have a cross-sectional shape in a plane perpendicular to the longitudinal axis which is trapezoidal, rectangular or radiused.

11. The surgical component of claim 1, wherein the elongate stem is tapered to be wider at its proximal end than at its distal end.

12. The surgical component of claim 1, wherein the component is:
a femoral implant,
a humeral implant,
a trial component; or
a broach.

13. A surgical kit including a surgical component, the surgical component comprising:
a body portion;
an elongate stem for inserting into an intramedullary canal of a patient, wherein the elongate stem extends distally from the body portion and has:
a longitudinal axis;
a proximal end;
a distal end; and
a plurality of splines located on an outer surface of the stem, wherein the splines are circumferentially arranged around the stem, and wherein at least some of the splines are tapered such that each tapered spline is narrower at a distal part of that spline than at a part of that spline that is proximal with respect to the distal part;
a plurality of further splines circumferentially arranged around the stem wherein the splines are wider than the further splines for a majority of the length of the splines; and
an elongate neck portion extending from the body portion at a non-zero angle with respect to the longitudinal axis of the stem.

14. A surgical method comprising using a surgical component, the surgical component comprising:
a body portion;
an elongate stem for inserting into an intramedullary canal of a patient, wherein the elongate stem extends distally from the body portion and has:
a longitudinal axis;
a proximal end;
a distal end; and
a plurality of splines located on an outer surface of the stem, wherein the splines are circumferentially arranged around the stem, and wherein at least some of the splines are tapered such that each tapered spline is narrower at a distal part of that spline than at a part of that spline that is proximal with respect to the distal part;
a plurality of further splines circumferentially arranged around the stem wherein the splines are wider than the further splines for a majority of the length of the splines; and
an elongate neck portion extending from the body portion at a non-zero angle with respect to the longitudinal axis of the stem,
the method comprising:
inserting the elongate stem into an intramedullary canal of a patient.

15. The surgical method of claim 14, further comprising receiving haptic feedback while inserting the stem into the intramedullary canal, wherein the haptic feedback is associated with increasing resistance to insertion provided by the tapered splines as the stem is inserted.

16. The surgical method of claim 14, wherein each spline has a distal end and a proximal end, and wherein at least some of the tapered splines each taper along their full length from the proximal and to the distal end thereof.

17. The surgical method of claim 14, wherein at least some of the tapered splines each have a distal region and a proximal region, wherein:
those splines are tapered in their distal region and have a constant width in their proximal region; or
those splines are tapered in their proximal region and have a constant width in their distal region.

18. The surgical method of claim 17, wherein in each spline having a tapered part and a part having a constant width, an interface between the distal region and the proximal region proximal region of that spline is located proximally with respect to a fixation region of the stem.

19. The surgical method of claim 14, wherein during said insertion of the stem into the intramedullary canal, the further splines come into contact with bone defining sidewalls of the intramedullary canal immediately prior to achieving a desired seating depth of the component.

20. The surgical method of claim 14, wherein the splines are narrower than the further splines for a majority of the length of the splines.

21. The surgical method of claim 14, wherein the splines and further splines are alternately arranged around a circumference of the stem.

22. The surgical method of claim 14, wherein at least some of the further splines have a constant width along their full length.

23. The surgical method of claim 14, wherein at least some of the further splines are tapered such that each tapered further spline is narrower at a distal part of that further spline than at a part of that further spline that is proximal with respect to the distal part.

24. The surgical method of claim 14, wherein the further splines are taller than the splines, measured from the longitudinal axis.

25. The surgical method of claim 14, wherein the further splines are less tall than the splines, measured from the longitudinal axis.

26. The surgical method of claim 14, wherein at least some of the splines and/or further splines have a cross-sectional shape in a plane perpendicular to the longitudinal axis which is trapezoidal, rectangular or radiused.

27. The surgical of claim 14, wherein the elongate stem is tapered to be wider at its proximal end than at its distal end.

28. The surgical method of claim 14, wherein the surgical component is a trial implant or a broach.

29. The surgical method of claim 14, wherein the surgical component is a femoral implant, and wherein the method comprises inserting the stem into an intramedullary canal of a femur.

30. The surgical method of claim 14, wherein the surgical component is a humeral implant, and wherein the method comprises inserting the stem into an intramedullary canal of a humerus.

* * * * *